United States Patent
Huang et al.

(10) Patent No.: US 10,279,202 B2
(45) Date of Patent: May 7, 2019

(54) PEPTIDE FOR PROMOTING HAIR GROWTH

(71) Applicant: H&H GROUP CO., LTD., Taipei (TW)

(72) Inventors: Min-Chuan Huang, Taipei (TW); Hsiao-Yu Chen, Taipei (TW); Syue-Ting Chen, Taipei (TW); He Xu, Taipei (TW); Pun Tsui, Taipei (TW)

(73) Assignee: H&H GROUP CO., LTD., Taipei, Taiwan (CN)

( * ) Notice: Subject to any disclaimer, the term of this patent is extended or adjusted under 35 U.S.C. 154(b) by 31 days.

(21) Appl. No.: 15/615,211

(22) Filed: Jun. 6, 2017

(65) Prior Publication Data
US 2018/0064965 A1 Mar. 8, 2018

(30) Foreign Application Priority Data
Sep. 7, 2016 (TW) .............................. 105128864 A

(51) Int. Cl.
| | |
|---|---|
| *A61K 38/10* | (2006.01) |
| *A61K 8/64* | (2006.01) |
| *C07K 4/12* | (2006.01) |
| *A61Q 7/00* | (2006.01) |
| *A61K 38/02* | (2006.01) |
| *A61K 38/17* | (2006.01) |

(52) U.S. Cl.
CPC .................. *A61Q 7/00* (2013.01); *A61K 8/64* (2013.01); *A61K 38/02* (2013.01); *A61K 38/1709* (2013.01); *C07K 4/12* (2013.01)

(58) Field of Classification Search
None
See application file for complete search history.

(56) References Cited

PUBLICATIONS

Morgan, The Dermal Papilla: An Instructive Niche for Epithelial Stem and Progenitor Cells in Development and Regeneration of the Hair Follicle, Cold Spring Harbor Perspectives in Medicine, 2014, 4:a015180, pp. 1-14.

*Primary Examiner* — Kevin S Orwig
(74) *Attorney, Agent, or Firm* — Rabin & Berdo, P.C.

(57) ABSTRACT

The present invention provides a peptide consisting of an amino acid sequence of SEQ ID NO: 1. Also provided is a method for promoting proliferation of a dermal papilla cell by incubating the cell with the peptide. Further provided is a method for promoting growth of a hair follicle in a skin by applying the peptide to the skin. Still provided is a method for preventing hair loss of a subject by administering the peptide to the subject. Yet further provided is a method for promoting hair growth of a subject by administering the peptide to the subject.

9 Claims, 5 Drawing Sheets
Specification includes a Sequence Listing.

PEPTIDE FOR PROMOTING HAIR GROWTH

CROSS REFERENCE

The non-provisional application claims priority from Taiwan Patent Application NO. 105128864, filed on Sep. 7, 2016, the content thereof is incorporated by reference herein.

FIELD OF THE INVENTION

The present invention is related to a peptide, and more particularly to a peptide for promoting hair growth.

BACKGROUND OF THE INVENTION

Minoxidil, spironolactone, and finasteride are active ingredients for hair growth in current use. Minoxidil and spironolactone are formulated in an external medicine for the treatment of hair loss/alopecia, and finasteride is formulated in an internal medicine for the treatment of hair loss/alopecia. However, a number of clinical trials have established these compounds can elicit side effects on a biological organism. For example, common side effects of minoxidil include burning or irritation of the eyes, and itching, redness, or irritation at the treated area; common side effects of spironolactone include electrolyte abnormalities (high blood potassium), nausea, vomiting, headache, rashes, and a decreased desire for sex; common side effects of finasteride include sexual dysfunction.

Therefore, it is desirable to develop a novel active ingredient for hair growth, and this novel active ingredient is derived from a natural product and has high biocompatibility to reduce the occurrence of side effects when applied to a biological organism.

SUMMARY OF THE INVENTION

The present invention is made according to an unexpected discovery that a certain amino acid fragment of human Mucin-15 protein can promote the proliferation of rat dermal papilla cells. Cold Spring Harb Perspect Med. 2014 July; 4(7): a015180, which is incorporated by reference herein, has stated that the proliferation of dermal papilla cells can lead to hair follicle growth and thus result in hair growth. Accordingly, it is understood that such discovered amino acid fragment also can promote the growth of hair follicles and hairs.

A first aspect of the present invention discloses a novel peptide, and the disclosed peptide consists of an amino acid sequence of SEQ ID NO: 1.

In certain embodiments, the peptide is obtained by protein isolation from a biological organism and then digestion, chemical synthesis, or genetic engineering.

A second aspect of the present invention discloses a method for promoting proliferation of a dermal papilla cell, and the disclosed method includes the step(s) of: incubating the dermal papilla cell with the foregoing peptide.

In certain embodiments, the peptide is formulated in a liquid form (e.g. a cell culture medium), a block form, a powder form, a gel form, or a foam form.

A third aspect of the present invention discloses a method for promoting growth of a hair follicle in a skin, and the disclosed method includes the step(s) of: applying the foregoing peptide to the skin.

In certain embodiments, the peptide is formulated in a liquid form (e.g. a hair follicle tissue growth medium), a block form, a powder form, a gel form, or a foam form.

A forth aspect of the present invention discloses a method for preventing hair loss of a subject, and the disclosed method includes the step(s) of: administering the foregoing peptide to the subject.

In certain embodiments, the peptide is formulated in a liquid form, a block form, a powder form, a gel form, or a foam form.

In some embodiments, the peptide is formulated in a cosmetic, an external medicine, an internal medicine, a food, or a drink.

In other embodiments, the cosmetic is a shampoo, a hair conditioner, a hair styling agent, a mascara, or a pet shampoo.

In further embodiments, the external medicine is a lotion, a cream, a gel, an oil, an ointment, a salve, an emulsion, a solution, or a suspension.

In additional embodiments, the internal medicine is a hard capsule, a soft capsule, a tablet, a syrup, a suspension, an emulsion, a solution, a solid dispersion, a wafer, or an elixir.

A fifth aspect of the present invention discloses a method for promoting hair growth of a subject, and the disclosed method includes the step(s) of: administering the foregoing peptide to the subject.

In certain embodiments, the peptide is formulated in a liquid form, a block form, a powder form, a gel form, or a foam form.

In some embodiments, the peptide is formulated in a cosmetic, an external medicine, an internal medicine, a food, or a drink.

In other embodiments, the cosmetic is a shampoo, a hair conditioner, a hair styling agent, a mascara, or a pet shampoo.

In further embodiments, the external medicine is a lotion, a cream, a gel, an oil, an ointment, a salve, an emulsion, a solution, or a suspension.

In additional embodiments, the internal medicine is a hard capsule, a soft capsule, a tablet, a syrup, a suspension, an emulsion, a solution, a solid dispersion, a wafer, or an elixir.

DETAILED DESCRIPTION OF THE INVENTION

The detailed description and preferred embodiments of the invention will be set forth in the following content, and provided for people skilled in the art so as to understand the characteristics of the invention.

Example 1

Peptide Preparation

Mucinhair peptide (sequence: NTSDPQKENRNTG) was synthesized by MDBio, Inc. (Taipei, Taiwan), and its purity (>75%) and composition were determined with high performance liquid chromatography (HPLC) and mass spectrometry (MS). Peptide stock was prepared by dissolving 10 mg of lyophilized peptide powder in 1 mL of double deionized water (ddH$_2$O), and then stored at −20° C.

Example 2

Isolation of Dermal Papilla Cells

Dermal papilla cells were isolated from rat whiskers and cells were cultured in Dulbecco's modified Eagle's medium (Thermo Scientific, Barrington, Ill., USA) with 10% fetal bovine serum (Gibco, Grand Island, N.Y., USA) and penicillin/streptomycin (100 IU/50 g/ml) in a humidified atmosphere containing 5% CO$_2$ at 37° C. Dermal papilla cells at the 3rd passage were used for all of the following experiments.

Example 3

Cell Proliferation Assay $2 \times 10^3$ dermal papilla cells were seeded in 96-well plates and incubated with Mucinhair peptide (50 µg/ml) or ddH$_2$O for the indicated period. 10 µL of 5 mg/mL 3-(4,5-dimethyl-2-thiazolyl)-2,5-diphenyl-2H-tetrazolium bromide solution (MTT; Sigma) was added to each well and incubated at 37° C. for 4 hours. After which, 100 µL of 10% SDS in 0.01N HCl was added to dissolve the MTT formazan crystals. The resultant optical density was measured spectrophotometrically at dual wavelengths, 550 and 630 nm. The MTT value was obtained by subtracting the OD$_{630}$ value from the OD$_{550}$ value.

Figure 1:
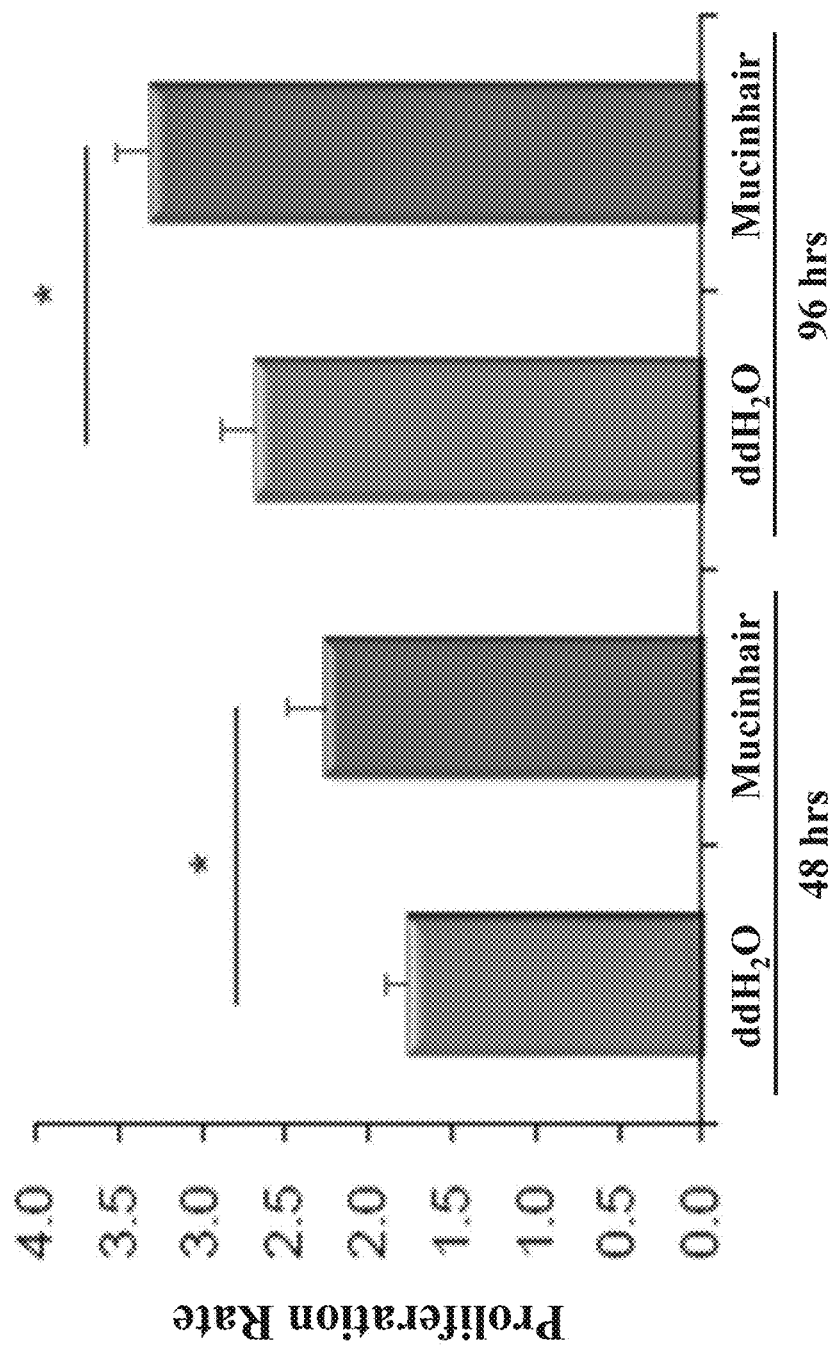
FIG. 1 is a bar graph illustrating the cell proliferation at the 48th hour or 96th hour after treatment.

The term "proliferation rate" used herein is defined as a quotient of the MTT value calculated from cells treated for an indicated period and that calculated from cells treated for 0 hour. As shown in FIG. 1, the proliferation rate of cells treated with ddH$_2$O for 48 hours is 1.77±0.12; the proliferation rate of cells treated with Mucinhair peptide for 48 hours is 2.26±0.23; the proliferation rate of cells treated with ddH$_2$O for 96 hours is 2.68±0.20; the proliferation rate of cells treated with Mucinhair peptide for 96 hours is 3.31±0.21.

As above, Mucinhair peptide has ability to promote dermal papilla cell proliferation.

Example 4

Hair Follicle Culture

Figure 2:
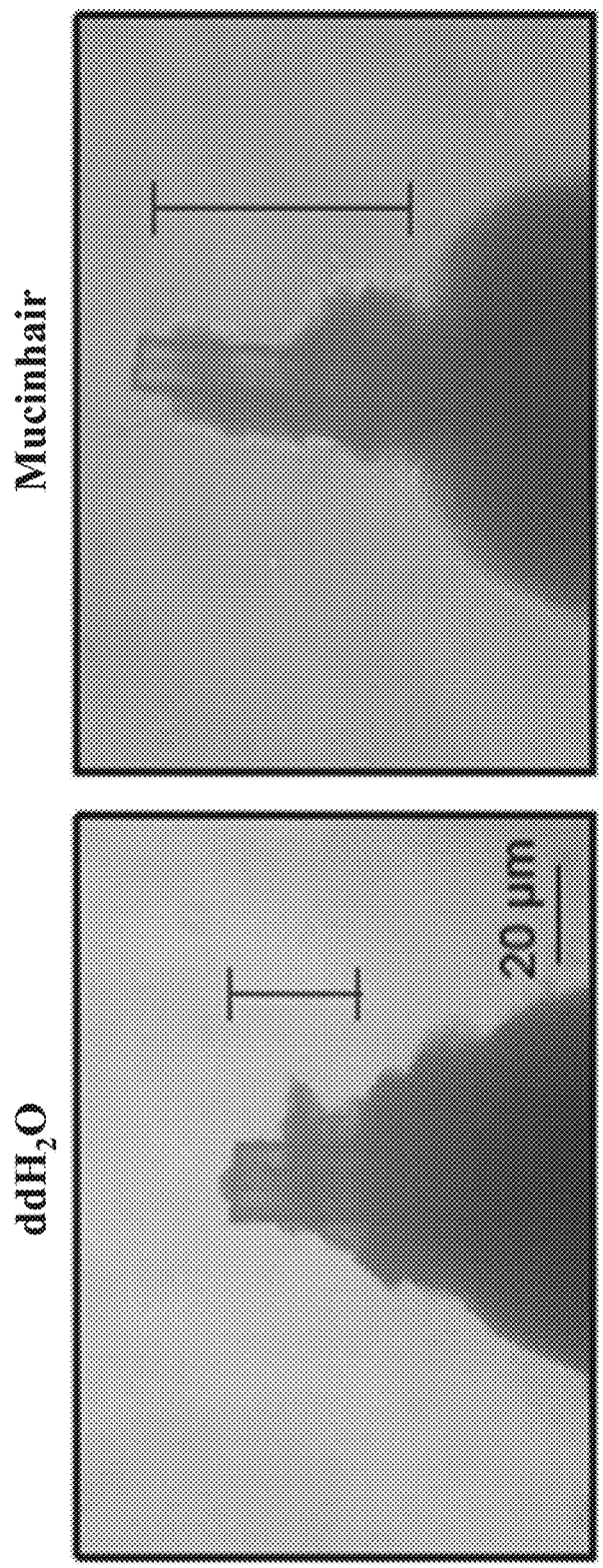
FIG. 2 is a microscopic picture showing hair shaft growth on the 20th day after treatment.
Figure 3:
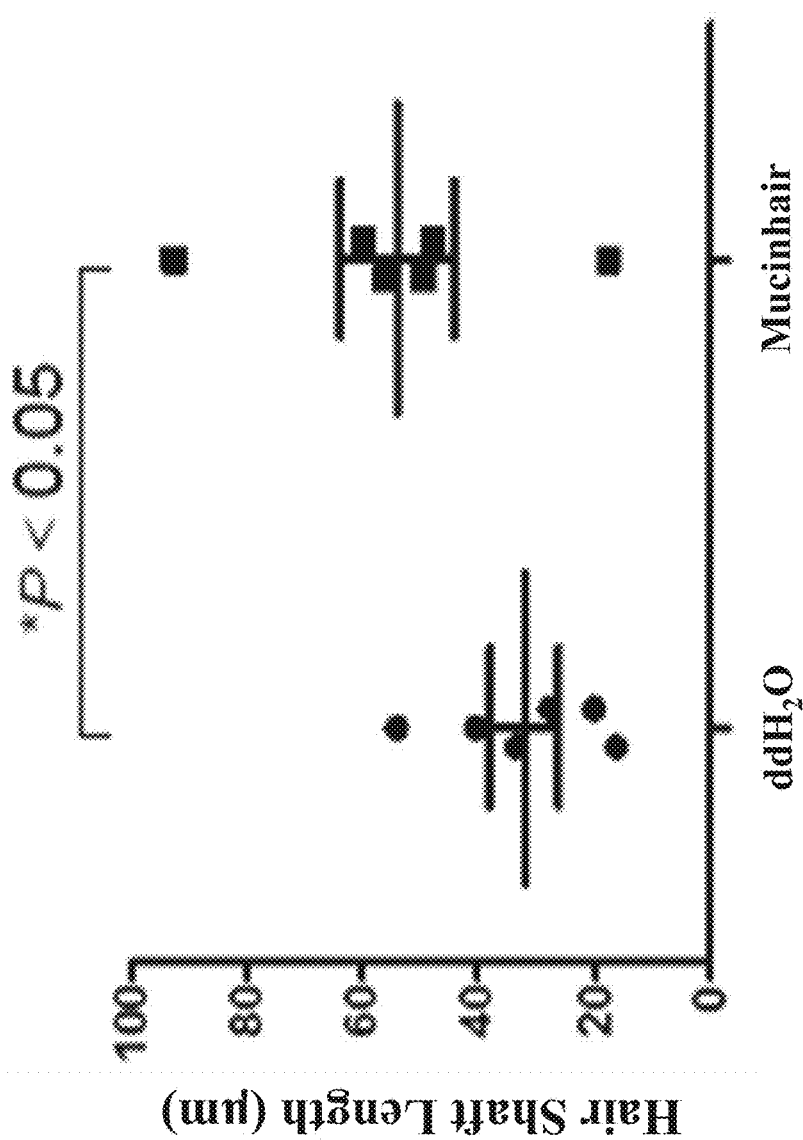
FIG. 3 is a statistical graph illustrating hair shaft lengths on the 20th day after treatment.

Hair follicles were isolated from 4 week-old rat whiskers and were maintained in Dulbecco's Modified Eagle Medium supplemented with 10% fetal bovine serum, 1% (v/v) antibiotic, and 250 ng/ml fungizone in 5% CO$_2$ at 37° C. for 24 hours. Then, the hair follicles were treated with ddH$_2$O or Mucinhair peptide (50 µg/ml). Medium was changed every 6 days and the hair shaft lengths were measured under a phase contrast microscope on the 20th day after the treatment. As shown in FIGS. 2 and 3, the hair shafts grown with Mucinhair peptide treatment are longer than those grown with ddH$_2$O treatment.

As above, Mucinhair peptide has ability to promote hair shaft elongation.

Example 5

Isolation of Epidermal Cells and Dermal Cells

Skin was peeled off from 1 day-old C57BL/6 mouse and its epidermis was separated from the dermis by 10 mg/ml Dispase digestion at 4° C. for 2 days. Epidermis and dermis were cut into small pieces and digested at 37° C. in 0.05% Trypsin-EDTA for 15 minutes and then 20 mg/ml collagenase for 60 minutes. Epidermal cells and dermal cells were collected through filtration with 70 µm strainers and low-speed centrifugation.

Example 6

Hair Patch Assay for Nude Mice $2 \times 10^7$ epidermal cells and $1 \times 10^8$ dermal cells were subcutaneously injected into nude mice with ddH$_2$O or Mucinhair peptide (50 µg/ml). After 30 days, mice were sacrificed and hair patch was excised and photographed. The excised skins were paraffin-embedded and tissues were sectioned and stained with hemmtoxylin and eosin (H&E).

Figure 4:
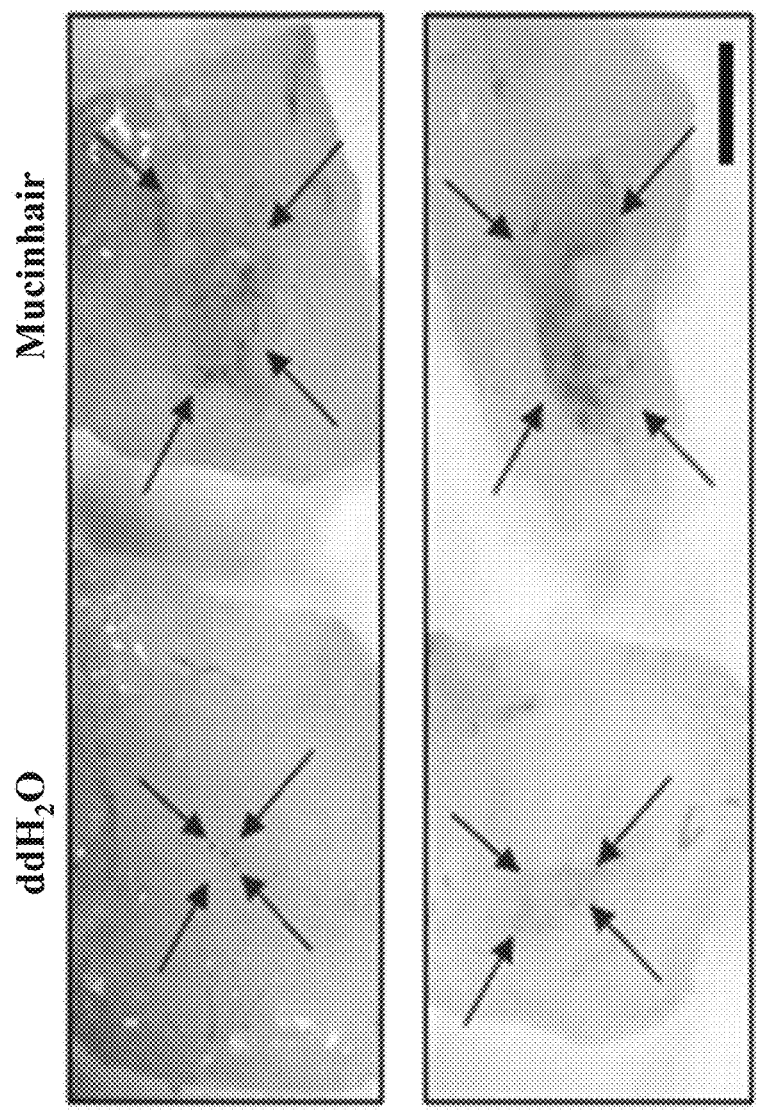
FIG. 4 is a microscopic picture showing hair growth of nude mice on the 30th day after injection.
Figure 5:
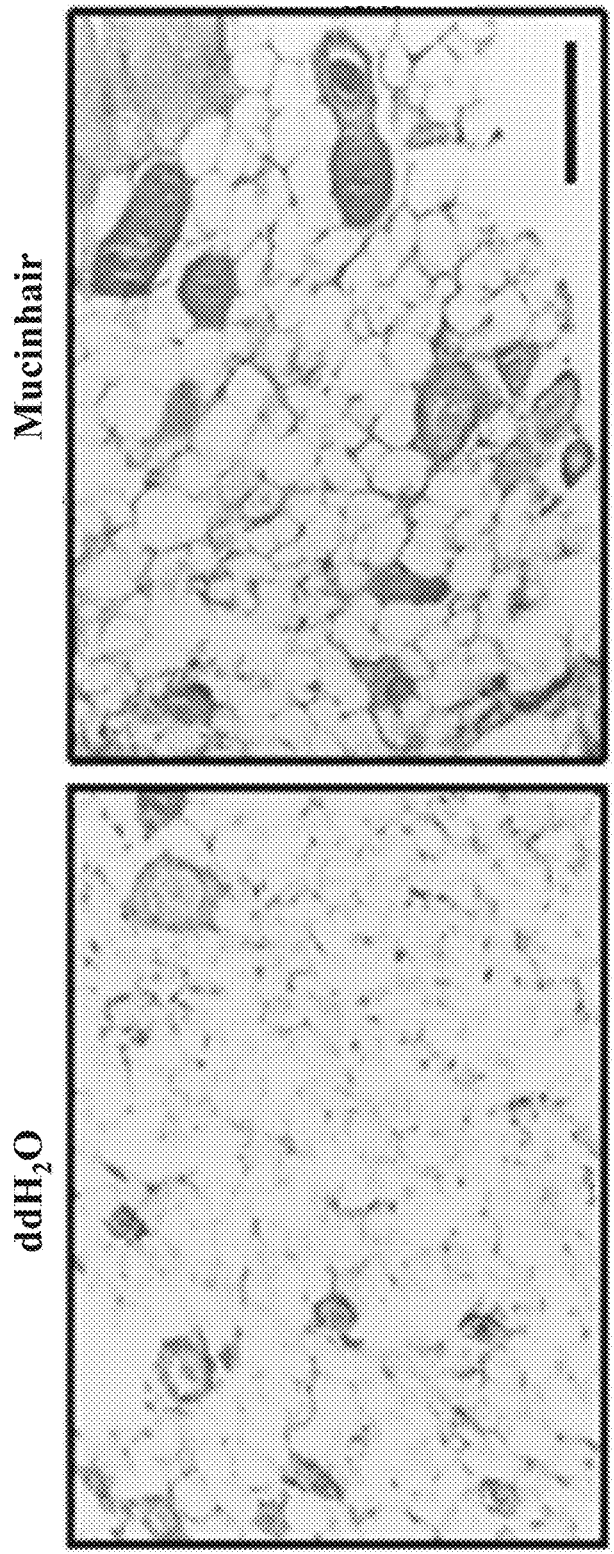
FIG. 5 is a microscopic picture showing hair follicles of nude mice on the 30th day after injection.

As shown in FIG. 4, what each arrow indicates is the region with hairs. Obviously, the region with hairs of nude mice injected with Mucinhair peptide is larger than that injected with ddH$_2$O. As further shown in FIG. 5, the hypodermis of nude mice injected with Mucinhair peptide has neogenic hair follicles.

As above, Mucinhair peptide has ability to promote hair follicle growth and hair growth in vivo.

While the invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

What is claimed is:

1. A method for promoting proliferation of a dermal papilla cell, comprising:

incubating the dermal papilla cell with a peptide consisting of the amino acid sequence of SEQ ID NO: 1.

2. The method as claimed in claim 1, wherein the peptide is formulated in a liquid form, a block form, a powder form, a gel form, or a foam form.

3. A method for promoting growth of a hair follicle in a skin, comprising:

applying a peptide consisting of the amino acid sequence of SEQ ID NO: 1 to the skin.

4. The method as claimed in claim 3, wherein the peptide is formulated in a liquid form, a block form, a powder form, a gel form, or a foam form.

5. A method for promoting hair growth of a subject, comprising:

applying a peptide consisting of the amino acid sequence of SEQ ID NO: 1 to the skin of the subject.

6. The method as claimed in claim 5, wherein the peptide is formulated in a liquid form, a block form, a powder form, a gel form, or a foam form.

7. The method as claimed in claim 5, wherein the peptide is formulated in a cosmetic or an external medicine.

8. The method as claimed in claim 7, wherein the cosmetic is a shampoo, a hair conditioner, a hair styling agent, a mascara, or a pet shampoo.

9. The method as claimed in claim 7, wherein the external medicine is a lotion, a cream, a gel, an oil, an ointment, a salve, an emulsion, a solution, or a suspension.

* * * * *

SEQUENCE LISTING

<160> NUMBER OF SEQ ID NOS: 1

<210> SEQ ID NO 1
<211> LENGTH: 13
<212> TYPE: PRT
<213> ORGANISM: Artificial
<220> FEATURE:
<223> OTHER INFORMATION: Synthetic

```
<400> SEQUENCE: 1

Asn Thr Ser Asp Pro Gln Lys Glu Asn Arg Asn Thr Gly
1               5                   10
```